(12) United States Patent
Kim et al.

(10) Patent No.: US 7,462,732 B2
(45) Date of Patent: Dec. 9, 2008

(54) VOLATILE NICKEL AMINOALKOXIDE COMPLEX AND DEPOSITION OF NICKEL THIN FILM USING SAME

(75) Inventors: Yunsoo Kim, Daejeon (KR); Chang-Gyoun Kim, Daejeon (KR); Young-Kuk Lee, Daejeon (KR); Taek-Mo Chung, Daejeon (KR); Ki-Seok An, Daejeon (KR); Sun-Sook Lee, Daejeon (KR); Seung-Ho Yoo, Kyungki-do (KR); Kiwhan Sung, Incheon (KR)

(73) Assignee: Korea Research Institute of Chemical Technology (KR)

( * ) Notice: Subject to any disclaimer, the term of this patent is extended or adjusted under 35 U.S.C. 154(b) by 0 days.

(21) Appl. No.: 11/910,693

(22) PCT Filed: Apr. 7, 2005

(86) PCT No.: PCT/KR2005/001002

§ 371 (c)(1),
(2), (4) Date: Oct. 4, 2007

(87) PCT Pub. No.: WO2006/107121

PCT Pub. Date: Oct. 12, 2006

(65) Prior Publication Data

US 2008/0171890 A1   Jul. 17, 2008

(51) Int. Cl.
*C07F 15/00* (2006.01)
*C23C 16/00* (2006.01)
(52) U.S. Cl. .................... 556/146; 427/248.1; 427/250
(58) Field of Classification Search ................ 556/146; 427/248.1, 250
See application file for complete search history.

(56) References Cited

OTHER PUBLICATIONS

Werndrup et al., Polyhedron, vol. 20, pp. 2163-2169 (2001).*
Hubert-Pfalzgraf et al., Polyhedron, vol. 16, No. 24, pp. 4197-4203 (1997).*
Seisenbaeva et al., New J. Chem., vol. 27, pp. 1059-1064 (2003).*
Park et al., Inorganic Chemistry Communications, vol. 7, pp. 463-466 (2004).*
Yang et al., J. Vac. Sci. Technol. A., vol. 23, No. 4, pp. 1238-1243 (Jul./Aug. 2005).*

* cited by examiner

*Primary Examiner*—Porfirio Nazario Gonzalez
(74) *Attorney, Agent, or Firm*—Baker & Hostetler, LLP

(57) ABSTRACT

A volatile nickel aminoalkoxide complex of formula (I) can form a nickel thin film having an improved quality by metal organic chemical vapor deposition (MOCVD).

7 Claims, 16 Drawing Sheets

(a) 250 °C (b) 300 °C (c) 350 °C (d) 400 °C (e) 450 °C (f) 500 °C (a) 270 °C (b) 290 °C (c) 300 °C (d) 310 °C (e) 330 °C (f) 350 °C

VOLATILE NICKEL AMINOALKOXIDE COMPLEX AND DEPOSITION OF NICKEL THIN FILM USING SAME

FIELD OF THE INVENTION

The present invention relates to a volatile nickel aminoalkoxide complex; a process of the preparation thereof; and a metal organic chemical vapor deposition (MOCVD) process for forming a nickel thin film on a substrate using said compound.

BACKGROUND OF THE INVENTION

Thin films of nickel, nickel alloys such as AuGeNi and $NiP_2$, nickel silicides, nickel gallides or nickel aluminides are widely used for the manufacture of semiconductor devices, nano-structures, hydrogen storage alloys and microelectromechanical actuators.

There have been reported studies of preparing such nickel-containing films by metal organic chemical vapor deposition (MOCVD) using nickel tetracarbonyl [$Ni(CO)_4$]; nickelocene compounds such as bis(cyclopentadienyl) nickel [$Ni(\eta^5-C_5H_5)_2$] and bis(methylcyclopentadienyl) nickel [$Ni(\eta^5-CH_3C_5H_4)_2$]; nickel β-diketonate compounds such as $Ni(acac)_2$ (acac=2,4-pentanedionato) and $Ni(hfac)_2$ (hfac=1,1,1,5,5,5-hexafluoro-2,4-pentanedionato). In addition, there have been disclosed reports regarding an organonickel precursor containing two β-ketoimine or aminoalkoxide ligands with nitrogen donor moieties which are capable of forming dative bonds with nickel [J. D. Martin, P. Hogan, K. A. Abboud, K.-H. Dahmen, *Chem. Mater.*, 1998, 10, 2525; and L. G. Hubert-Pfalzgraf, H. Guillon, *Appl. Organomet. Chem.*, 1998, 12, 221].

However, $Ni(CO)_4$ is very toxic while the nickel β-ketoimine compound has relatively low volatility, and the above conventional precursors are known to give nickel thin films containing carbon and oxygen contaminants.

SUMMARY OF THE INVENTION

Accordingly, it is an object of the present invention to provide a novel organonickel compound which has high volatility and high thermal stability, and can be advantageously used in forming a nickel thin film of improved quality under a mild condition.

It is another object of the present invention to provide a process for preparing said compound.

It is a further object of the present invention to provide a process for depositing a nickel thin film on a substrate using said compound.

In accordance with one aspect of the present invention, there is provided a nickel aminoalkoxide complex of formula (I):

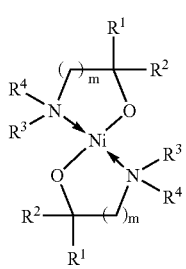  (I)

wherein, $R^1$, $R^2$, $R^3$ and $R^4$ are each independently linear or branched $C_{1-4}$ alkyl; and m is an integer in the range of 1 to 3.

In accordance with another aspect of the present invention, there is provided a process for preparing said nickel aminoalkoxide complex of formula (I) comprising reacting a compound of formula (II) with a compound of formula (III) or reacting a compound of formula (IV) with a compound of formula (V), in an organic solvent:

$Ni(OY)_2$     (II)

$HOCR^1R^2(CH_2)_mNR^3R^4$     (III)

$Ni(NH_3)_6X_2$     (IV)

$MOCR^1R^2(CH_2)_mNR^3R^4$     (V)

wherein, X is halogen; Y is $C_{1-4}$ alkyl; M is Li or Na; and $R^1$, $R^2$, $R^3$, $R^4$ and m are the same as previously defined.

In accordance with further another aspect of the present invention, there is provided a process for depositing a nickel thin film on a substrate which comprises bringing the vapor of the nickel aminoalkoxide complex of formula (I) into contact with a substrate heated to a temperature ranging from 200 to 500° C.

BRIEF DESCRIPTION OF THE DRAWINGS

The above and other objects and features of the present invention will become apparent from the following description of the invention taken in conjunction with the following accompanying drawings, which respectively show.

DETAILED DESCRIPTION OF THE INVENTION

Figure 1:
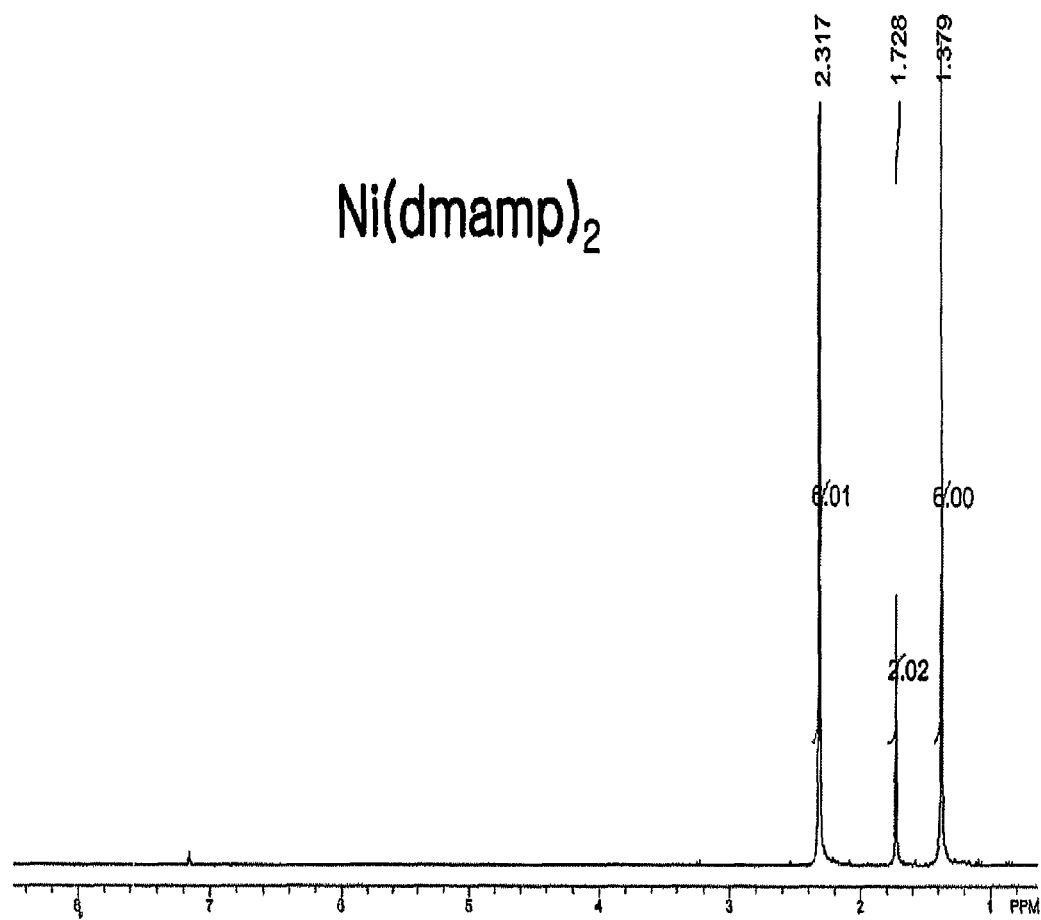
FIGS. 1 and 2: $^1$H nuclear magnetic resonance ($^1$H NMR) spectra of the nickel aminoalkoxide complexes prepared in Examples 1 and 2, respectively.

The novel compound of formula (I) of the present invention is a complex formed between two aminoalkoxide ligands and one divalent nickel ion, wherein the coordination of the nickel ion is saturated, and the two $C_{1-4}$ alkyl groups at the α-carbon and the two $C_{1-4}$ alkyl groups bonded to the amino-nitrogen atom serve to shield the oxygen and nitrogen atoms of the aminoalkoxide ligand. This minimizes the compounds' intermolecular interactions and confers on the compound a high affinity toward an organic solvent such as diethyl ether, tetrahydrofuran, toluene, hexane and a mixture thereof.

The inventive nickel complex is either a liquid or solid at room temperature, can be vaporized or sublimed at a low temperature in the range of 30 to 100° C., and undergoes facile and clean thermal decomposition to provide a contaminant-free nickel thin film under a mild condition when applied to an MOCVD process, while generating volatile hydrocarbon species through intramolecular β-hydrogen elimination.

Among the compounds of formula (I) of the present invention, the preferred are those wherein $R^1$, $R^2$, $R^3$ and $R^4$ are each independently $CH_3$, $C_2H_5$, $CH(CH_3)_2$ or $C(CH_3)_3$, and m is 1 or 2.

The inventive complex of formula (I) may be prepared by reacting a compound of formula (II) with a compound of formula (III) in an organic solvent such as toluene under a refluxing condition, as shown in Reaction Scheme A:

Reaction Scheme A

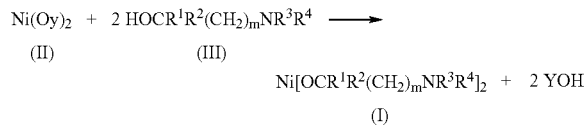

wherein, $R^1$, $R^2$, $R^3$, $R^4$, m and Y have the same meanings as defined above.

Alternatively, the inventive complex of formula (I) may be prepared by reacting a compound of formula (IV) with a compound of formula (V) in an organic solvent such as toluene under a refluxing condition, as shown in Reaction Scheme B:

Reaction Scheme B

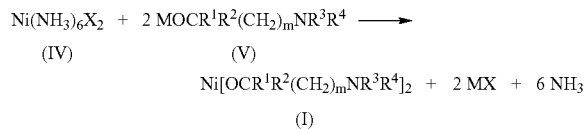

wherein, $R^1$, $R^2$, $R^3$, $R^4$, m, X and M have the same meanings as defined above.

As shown in Reaction Schemes A and B, the compound of formula (III) or (V) is reacted with the compound of formula (II) or (IV) in a stoichiometric ratio, e.g., in an amount of 2 equivalents based on 1 equivalent of the compound of formula (II) or (IV) to prepare the inventive nickel complex of formula (I).

In accordance with the present invention, a nickel thin film may be deposited on a substrate by bringing the vapor of the nickel aminoalkoxide complex of formula (I) into contact with a substrate heated to a temperature ranging from 200 to 500° C., preferably from 250 to 350° C.

The decomposition mechanism for the conversion of the inventive nickel complex into metallic nickel in such MOCVD is shown in Reaction Scheme C:

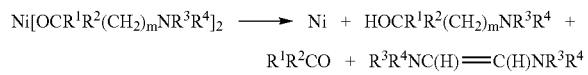

wherein, $R^1$, $R^2$, $R^3$, $R^4$ and m have the same meanings as defined above.

The inventive nickel complex converts to metallic nickel through intramolecular β-hydrogen elimination on decomposition, while generating volatile hydrocarbon species such as aminoalcohols, ketones and endiamines.

The substrate which may be used in practicing the present invention is any inorganic solid that is stable at or above the film deposition temperature and examples thereof include glass, quartz, silicon, gallium arsenide, sapphire, alkali metal niobate and alkaline earth metal titanate, among which a TiN- or TaN-coated single crystal of silicon is preferred when the coated substrate is intended for use in electronic applications.

The following Examples are given for the purpose of illustration only, and are not intended to limit the scope of the invention.

<Synthesis of Nickel Aminoalkoxide Complex of formula (I)>

EXAMPLE 1

Bis(dimethylamino-2-methyl-2-propoxo)nickel(II) [Ni(dmamp)$_2$]

3.50 g (15.10 mmol) of Ni(NH$_3$)$_6$Cl$_2$ was suspended in 50 mL of toluene in a 125 mL Schlenk flask and 4.62 g (33.20 mmol) of sodium dimethylamino-2-methyl-2-propoxide [Na(dmamp)] was slowly added thereto. The color of the mixed solution gradually changed to dark brown. The dark brown mixture was refluxed for 8 hours under a nitrogen atmosphere and filtered. The resulting filtrate was distilled in a vacuum to remove the solvent. The solid obtained was purified by sublimation at 60° C. under a reduced pressure of $10^{-2}$ Torr, to give 3.20 g of the title compound in the form of a dark brown solid having a melting point of 118-119° C. (yield: 72.9%).

$^1$H NMR (ppm, C$_6$D$_6$): 1.379 (s, 6H, —C(C$\underline{H}_3$)$_2$), 1.728 (s, 2H, —C$\underline{H}_2$), 2.317 (s, 6H, —N(C$\underline{H}_3$)$_2$) (see FIG. 1).

Elemental analysis: Calculated for C$_{12}$H$_{28}$N$_2$O$_2$Ni: C, 49.52; H, 9.70; N, 9.62. Found: C, 49.08; H, 9.45; N, 9.47.

Figure 3:
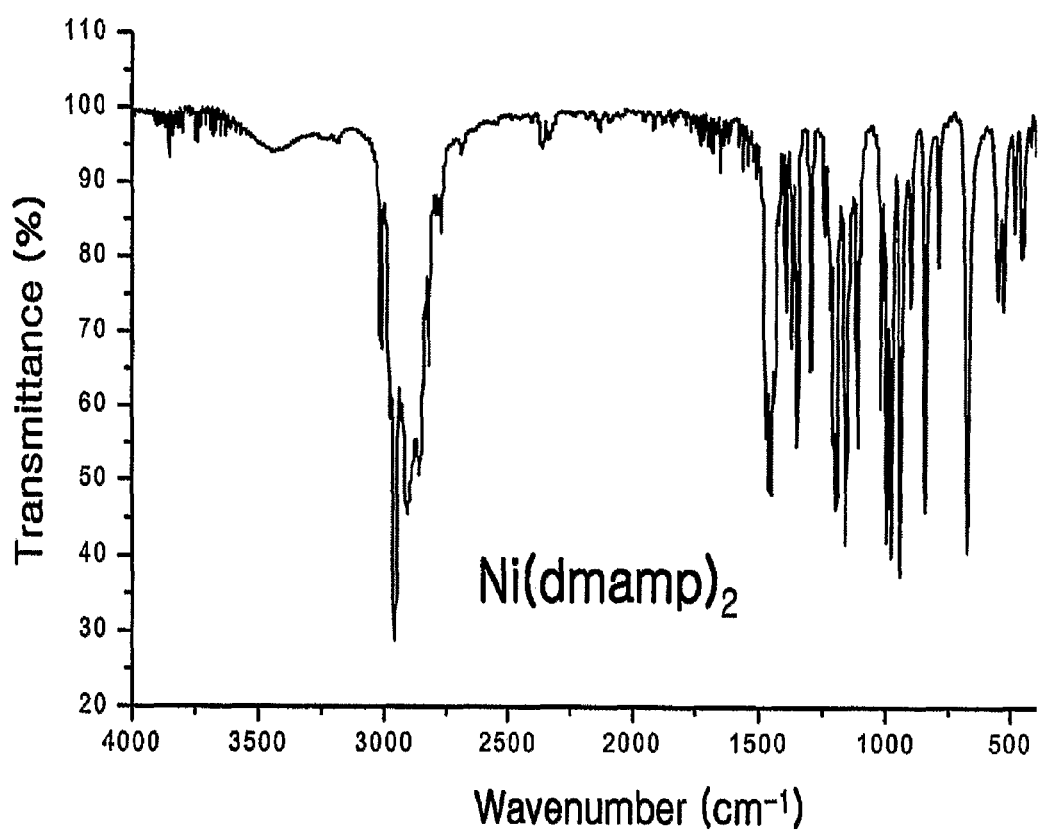
FIGS. 3 and 4: Fourier transform infrared (FT-IR) spectra of the nickel aminoalkoxide complexes prepared in Examples 1 and 2, respectively.

FT-IR (cm$^{-1}$, KBr pellet): ν(Ni—O) 551, 527, 453 (see FIG. 3).

Mass spectrometry (EI, 70 eV), m/z (ion, relative intensity): 290 ([Ni(L)$_2$]$^+$, 38), 232 ([Ni(L)$_2$-CH$_2$NMe$_2$]$^+$, 11), 217 ([Ni(L)$_2$-CH$_2$NMe$_2$-Me]$^+$, 14), 174 ([Ni(L)]$^+$, 100), 159 ([Ni(L)-Me]$^+$, 20), 116 ([Ni(L)-CH$_2$NMe$_2$]$^+$, 29), 58 ([CH$_2$NMe$_2$]$^+$, 77).

EXAMPLE 2

Bis(diethylamino-2-methyl-2-propoxo)nickel(II) [Ni(deamp)$_2$]

2.00 g (8.63 mmol) of Ni(NH$_3$)$_6$Cl$_2$ was suspended in 50 mL of toluene in a 125 mL Schlenk flask and 2.90 g (17.34 mmol) of sodium diethylamino-2-methyl-2-propoxide [Na(deamp)] was slowly added thereto. The color of the mixed solution gradually changed to dark brown. The dark brown mixture was refluxed for 8 hours under a nitrogen atmosphere and filtered. The resulting filtrate was distilled in a vacuum to remove the solvent. The solid obtained was purified by sublimation at 60° C. under a reduced pressure of $10^{-2}$ Torr, to give 1.85 g of the title compound in the form of a dark brown solid having a melting point of 54-55° C. (yield: 61.7%).

Figure 2:
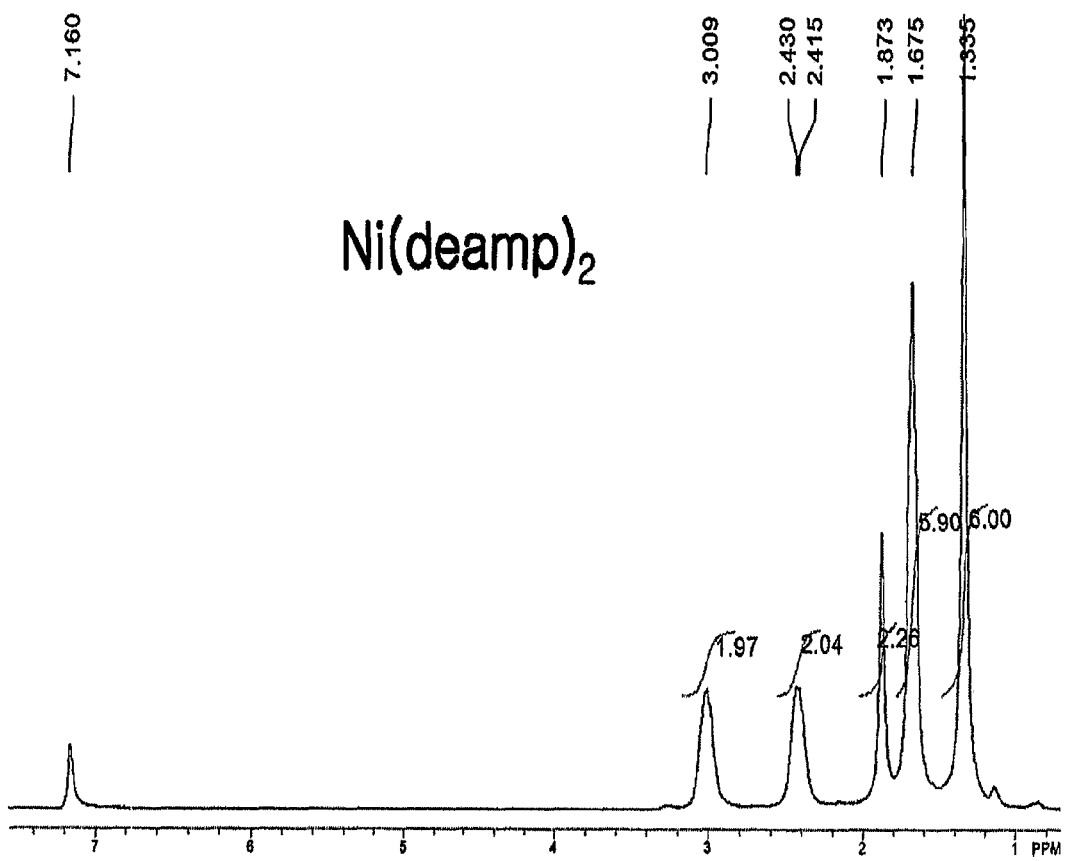

$^1$H NMR (ppm, C$_6$D$_6$): 1.335 (s, 6H, —C(C$\underline{H}_3$)$_2$), 1.675 (s, br, 6H, —N(CH$_2$C$\underline{H}_3$)), 1.873 (s, 2H, —C$\underline{H}_2$), 2.422, 3.009 (s, br 4H, —N(C$\underline{H}_2$CH$_3$)) (see FIG. 2).

Elemental analysis: Calculated for C$_{16}$H$_{36}$N$_2$O$_2$Ni: C, 55.35; H, 10.45; N, 8.07. Found: C, 50.95; H, 9.69; N, 8.60.

Figure 4:
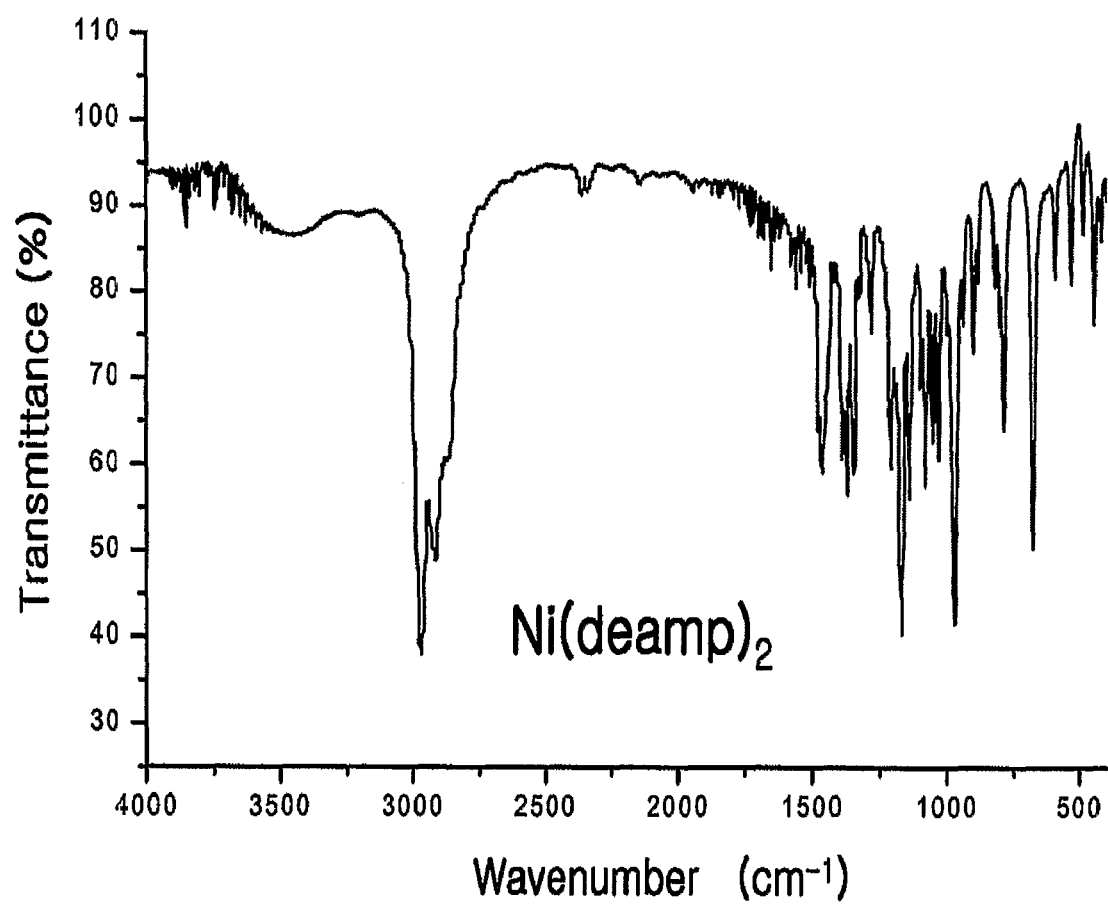

FT-IR (cm$^{-1}$, KBr pellet): ν(Ni—O) 592, 531, 443 (see FIG. 4).

Mass spectrometry (EI, 70 eV), m/z (ion, relative intensity): 346 ([Ni(L)$_2$]$^+$, 16), 230 ([Ni(L)$_2$-CH$_2$NEt$_2$-Me$_2$]$^+$, 25), 202 ([Ni(L)]$^+$, 39), 130 ([Ni(L)-NEt$_2$]$^+$, 44), 86 ([L-Et$_2$]$^+$, 100), 58 ([OCMe$_2$]$^+$, 45).

EXAMPLE 3

Bis(dimethylamino-2-methyl-2-butoxo)nickel(II) [Ni(dmamb)$_2$]

4.50 g (19.3 mmol) of Ni(NH$_3$)$_6$Cl$_2$ was suspended in 50 mL of toluene in a 125 mL Schlenk flask and 6.00 g (38.6 mmol) of sodium dimethylamino-2-methyl-2-butoxide [Na (dmamb)] was slowly added thereto. The color of the mixed solution gradually changed to dark brown. The dark brown mixture was refluxed for 8 hours under a nitrogen atmosphere and filtered. The resulting filtrate was distilled in a vacuum to remove the solvent. The liquid residue was purified by sublimation at 80° C. under a reduced pressure of 10$^{-2}$ Torr, to give 5.07 g of the title compound in the form of a green liquid (yield: 82.6%).

$^1$H NMR (ppm, C$_6$D$_6$): 0.93 (t, J=7.6 Hz, 6H, —CH$_2$C$\underline{H}_3$), 1.35 (d, J=3.6 Hz, 6H, —C(C$\underline{H}_3$)), 1.65 (m, 4H, —C$\underline{H}_2$CH$_3$), 1.81 (m, 4H, —NCH$_2$C—), 2.29 (d, J=7.5 Hz, 6H, —N(C $\underline{H}_3$)$_2$), 2.38 (d, J=8.7 Hz, 6H, —N(C$\underline{H}_3$)$_2$).

$^{13}$C NMR ppm, C$_6$D$_6$): 9.7, 28.9, 37.5, 51.1, 75.2, 75.9.

Elemental analysis: Calculated for C$_{14}$H$_{32}$N$_2$O$_2$Ni: C, 52.69; H. 10.11; N, 8.78. Found: C, 52.33; H, 10.50; N, 9.84.

FT-IR (cm$^{-1}$, KBr pellet): ν(Ni—O) 555, 492, 451.

Mass spectrometry (EI, 70 eV), m/z (ion, relative intensity): 318 ([Ni(L)$_2$]$^+$, 100), 289 ([Ni(L)$_2$-CH$_2$CH$_3$]$^+$, 78), 231 ([Ni(L)$_2$-CH$_2$CH$_3$—C(O)(Me)(Et)]$^+$, 61), 188 ([Ni(L)]$^+$, 74), 159 ([Ni(L)-CH$_2$CH$_3$]$^+$, 30), 58 ([CH$_2$NMe$_2$]$^+$, 79).

Figure 5:
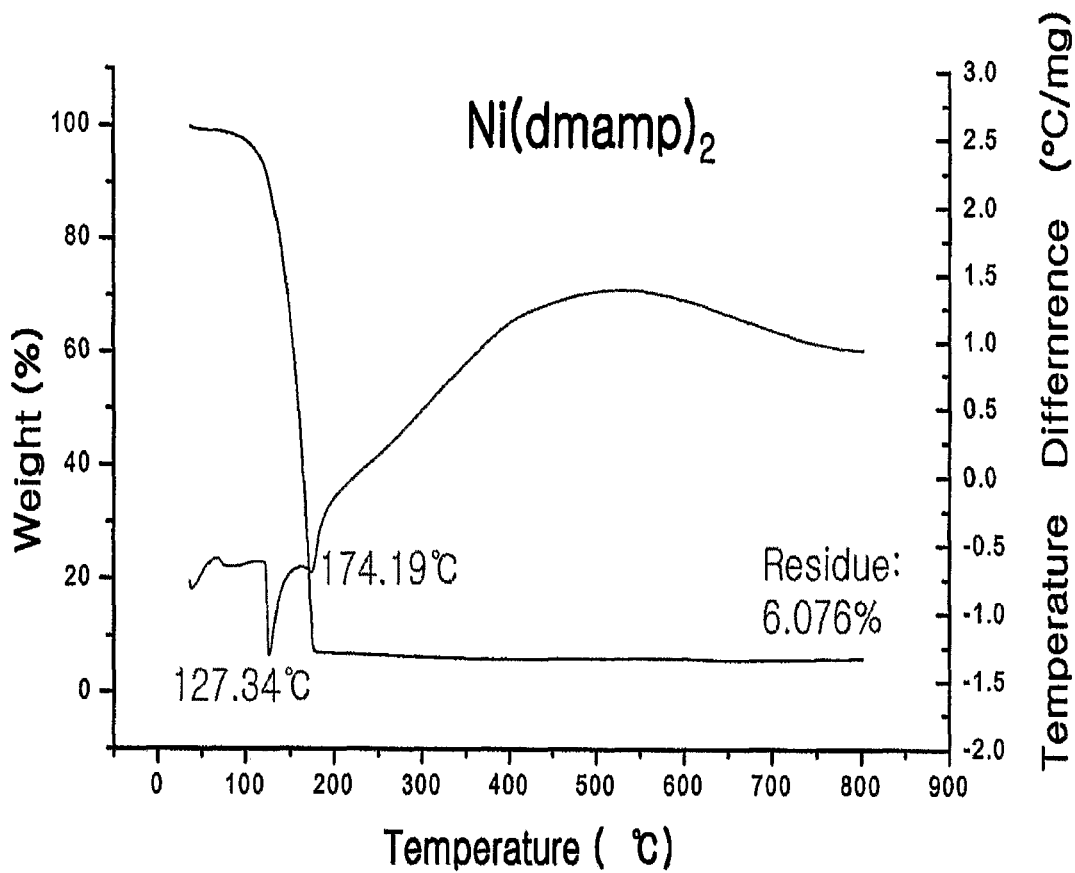
FIGS. 5 to 7: Thermogravimetric/differential thermal analysis (TG/DTA) scans of the nickel aminoalkoxide complexes prepared in Examples 1 to 3, respectively.
Figure 6:
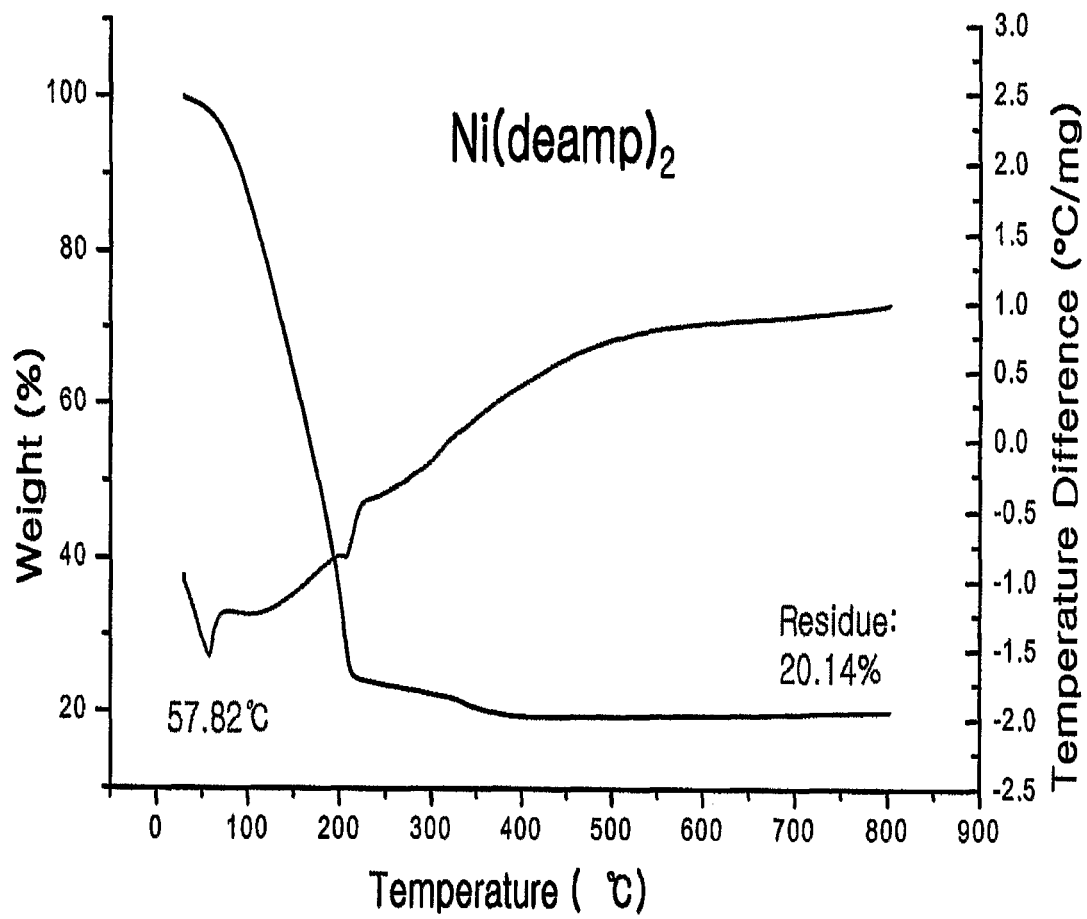
Figure 7:
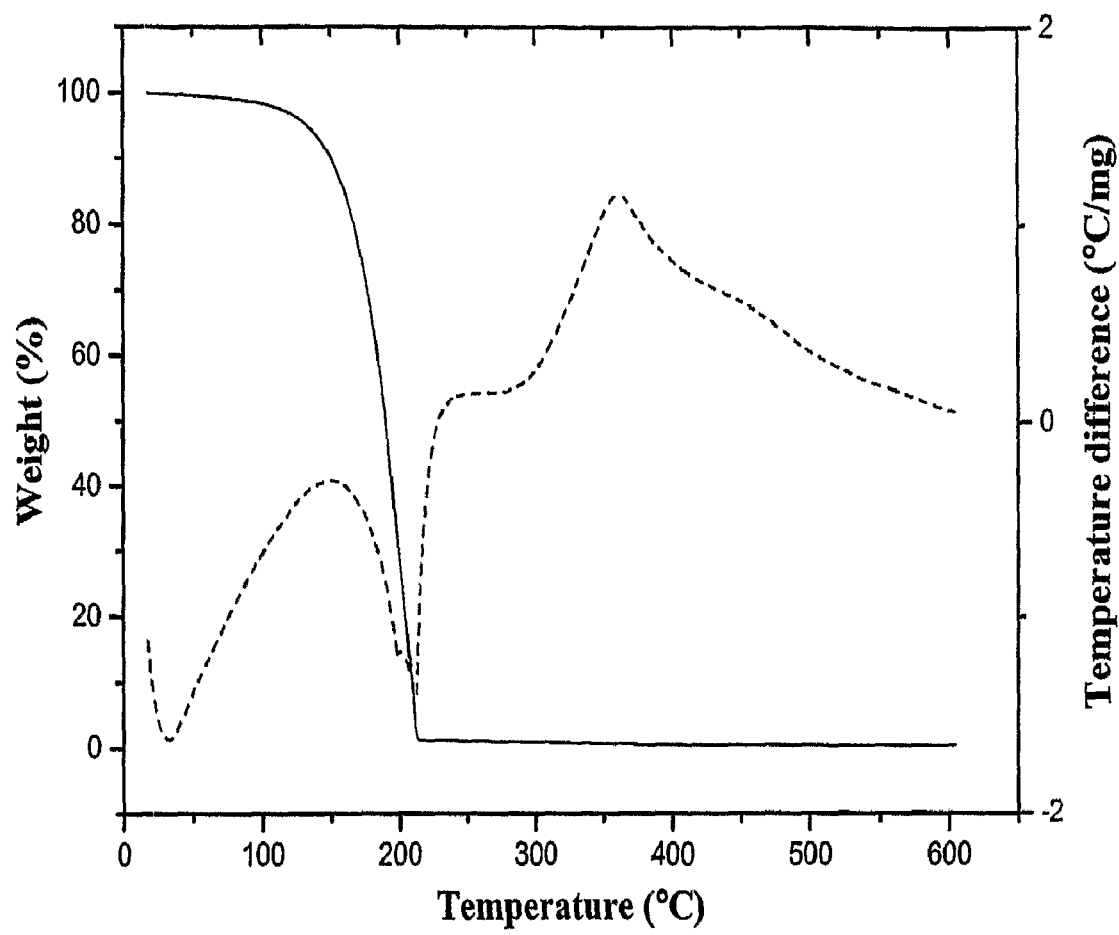

Thermogravimetric/differential thermal analysis (TG/DTA) scans of the nickel aminoalkoxide complexes prepared in Examples 1 and 3 are shown in FIGS. 5 to 7, respectively. The TGA results revealed that Ni(dmamp)$_2$, Ni(deamp)$_2$ and Ni(dmamb)$_2$ each underwent an abrupt weight loss in the temperature range 100 to 200° C., and also that T$_{1/2}$ (the temperature at which the weight of the sample was reduced to half) of Ni(dmamp)$_2$, Ni(deamp)$_2$ and Ni(dmamb)$_2$ were 150° C., 170° C. and 185° C., respectively. DTA scans showed that they all have endothermic peaks due to decomposition around 200° C.

These results suggest that the nickel complexes synthesized in Examples 1 to 3 have high volatility, are thermally stable and convert to relatively pure nickel on decomposition, and therefore, they are suitable MOCVD precursors for nickel deposition.

<Deposition of Nickel Thin Film>

EXAMPLE 4

A Si(001) wafer having an oxide layer on its surface was heated to a temperature selected from 200, 250, 300 and 350° C. at an initial pressure of 10$^{-5}$ Torr. Ni(dmamp)$_2$ prepared in Example 1 was vaporized at 60° C. and the vapor was transported to the surface of the wafer using an argon carrier gas (flow rate 4 sccm) at a total pressure of 10 mTorr to deposit a film thereon.

Figure 8A:
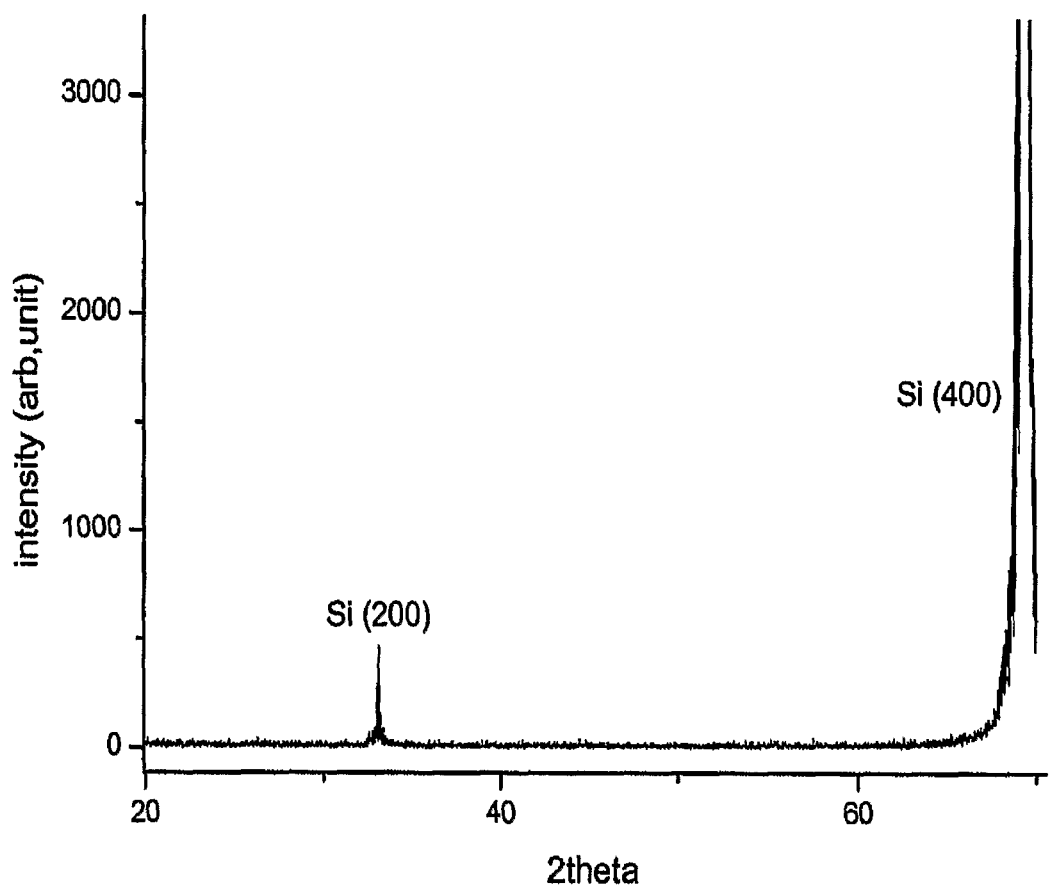
FIGS. 8A, 8B and 8C: X-ray diffraction (XRD) patterns (FIGS. 8A and 8B) and a scanning electron microscopy (SEM) image (FIG. 8C) of the nickel thin films obtained in Example 4, respectively.
Figure 8B:
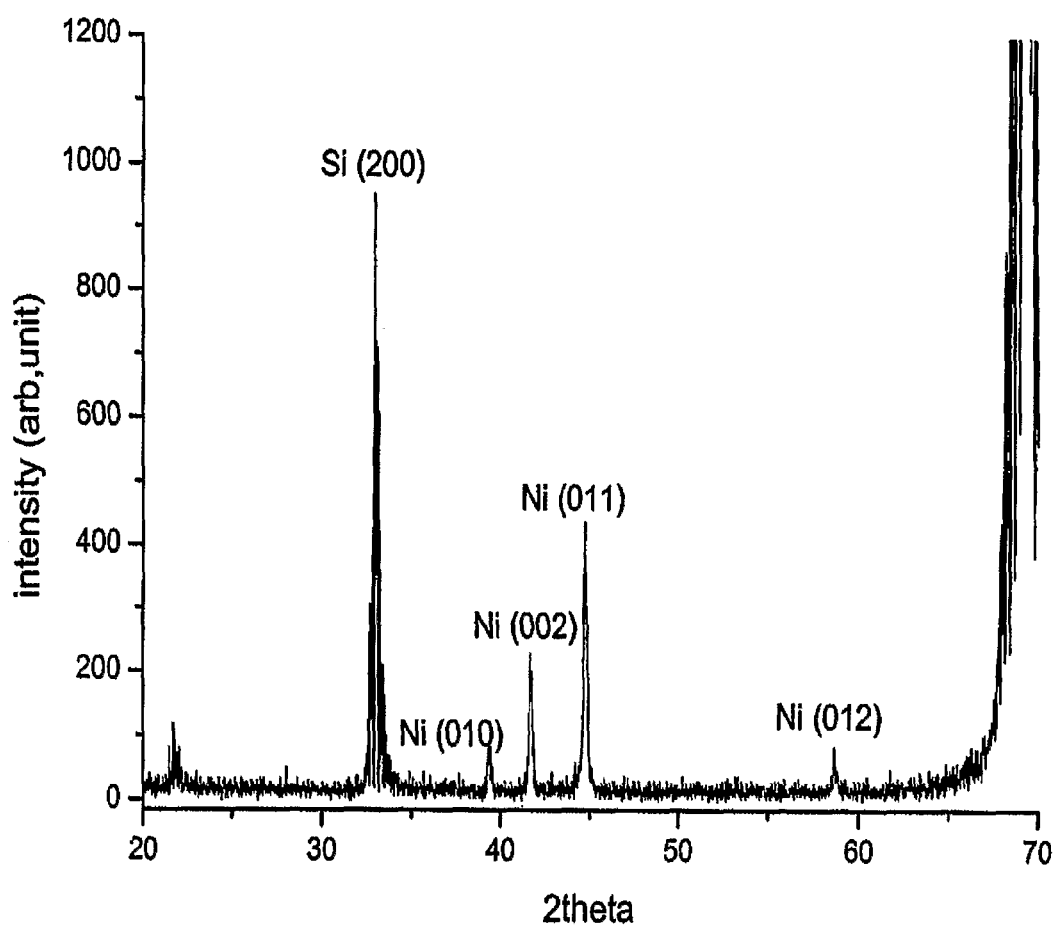
Figure 8C:
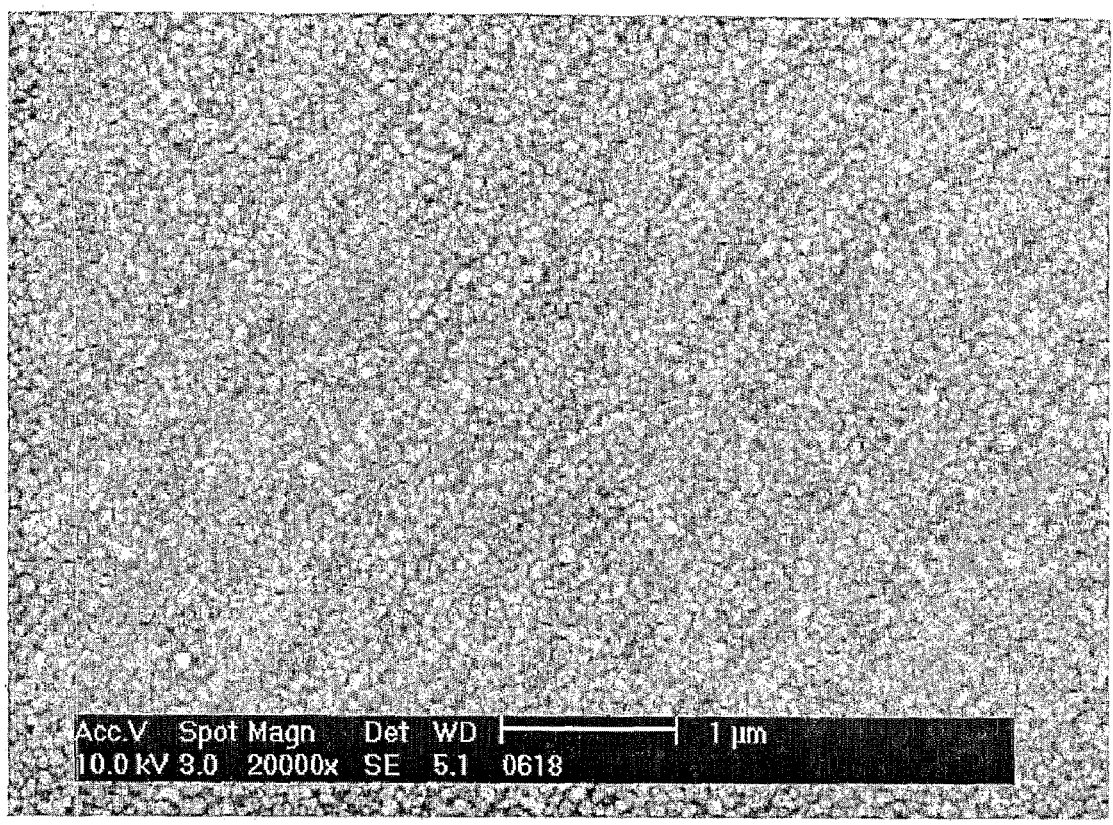

X-ray photoelectron spectra of the deposited films showed that the films were pure metallic nickel. XRD patterns thereof showed that the films deposited at 250-350° C. were crystalline (FIG. 8B: 250° C.), while the film deposited at 200° C. was non-crystalline (FIG. 8A). An SEM image of the film deposited at 250° C. shown in FIG. 8C revealed that it was composed of grains having a grain size of 100 nm or less.

EXAMPLE 5

A Si(001) wafer having an oxide layer on its surface was heated to a temperature selected from 250, 300, 350, 400, 450 and 500° C. at an initial pressure of 10$^{-3}$ Torr. Ni(dmamp)$_2$ prepared in Example 1 was vaporized at 60° C. and the vapor was transported to the surface of the wafer using an argon carrier gas (flow rate 4 sccm) at a total pressure of 100 mTorr to deposit a film thereon.

Figure 9A:
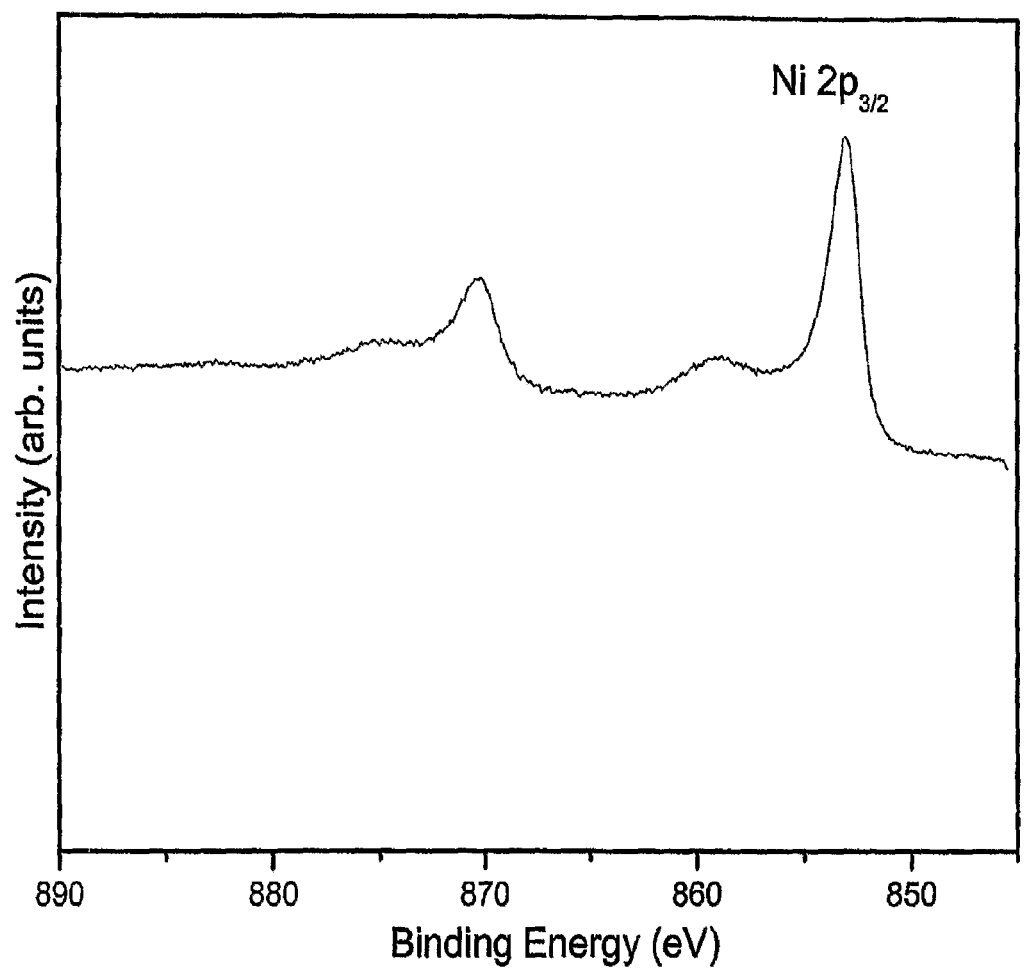
FIGS. 9A, 9B and 9C: X-ray photoelectron spectrum, XRD patterns and SEM images of the nickel thin films obtained in Example 5, respectively.
Figure 9B:
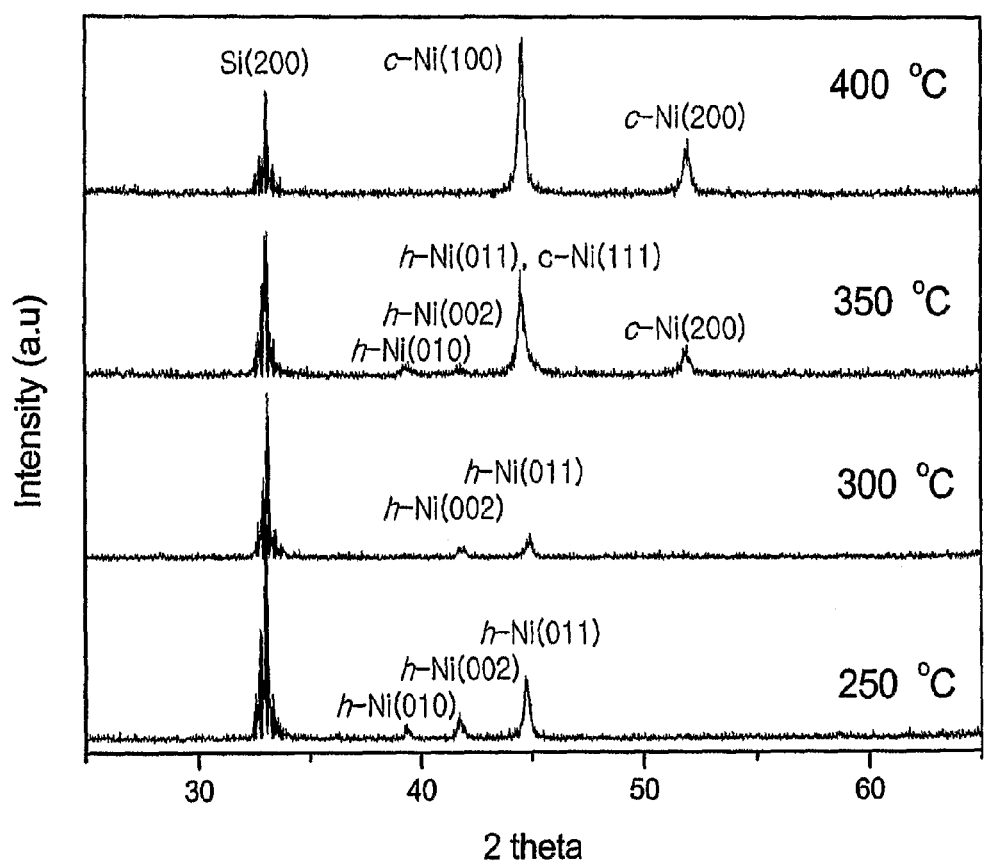
Figure 9C:
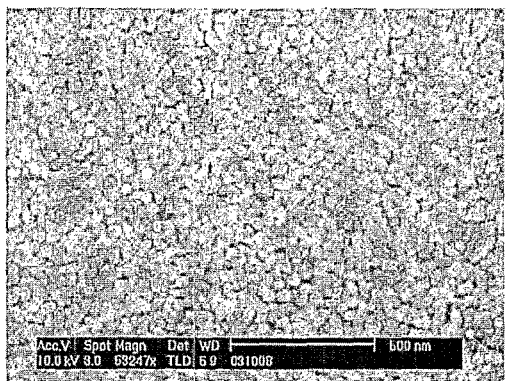
Figure 9C:
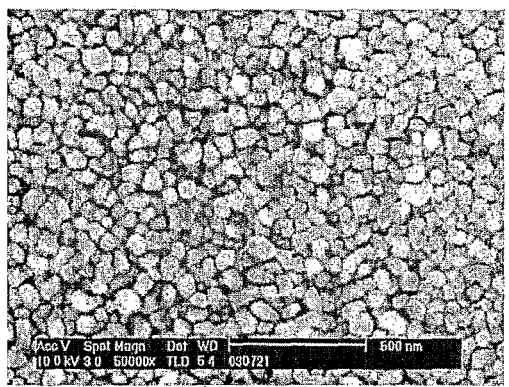
Figure 9C:
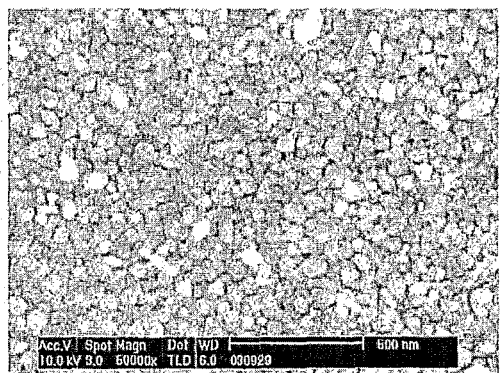
Figure 9C:
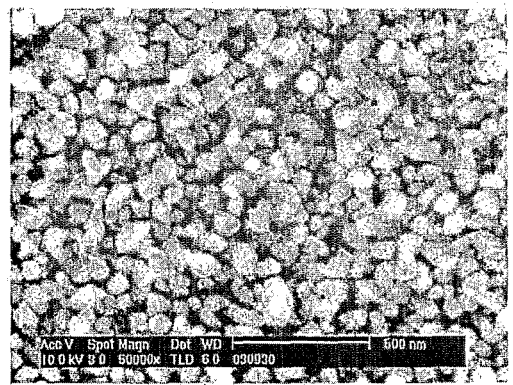
Figure 9C:
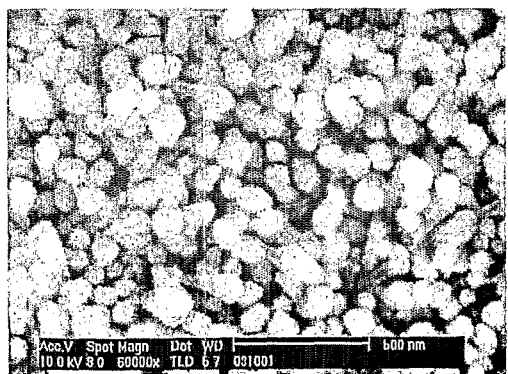
Figure 9C:
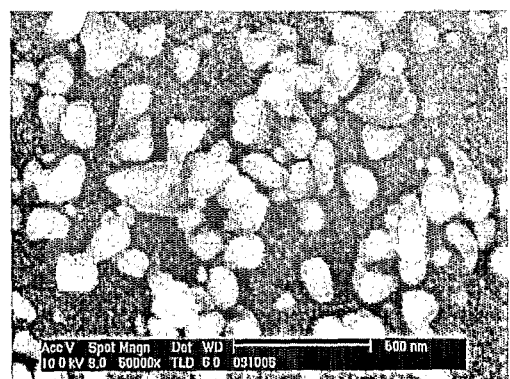

X-ray photoelectron spectra of the deposited films showed that the films were pure metallic nickel (FIG. 9A: 400° C.). XRD patterns thereof showed that the film deposited at 250° C. was non-crystalline, the film deposited at 300° C. was composed of hexagonal crystals, the film deposited at 350° C. was composed of cubic and hexagonal crystals, and the films deposited at 400-500° C. were composed of cubic crystals (FIG. 9B). SEM images of the films shown in FIG. 9C revealed that the growth at 250-350° C. provided highly dense films composed of grains having a grain size of 30-50 nm.

EXAMPLE 6

A Si(001) wafer having an oxide layer on its surface was heated to 300° C. at an initial pressure of 40 mTorr. Ni(dmamb)$_2$ prepared in Example 3 was vaporized at 40° C. and the vapor was transported to the surface of the wafer using an argon carrier gas (flow rate 10 sccm) together with a hydrogen gas flow (flow rate 10 sccm) at a total pressure of 70 mTorr to deposit a film thereon.

Figure 10:
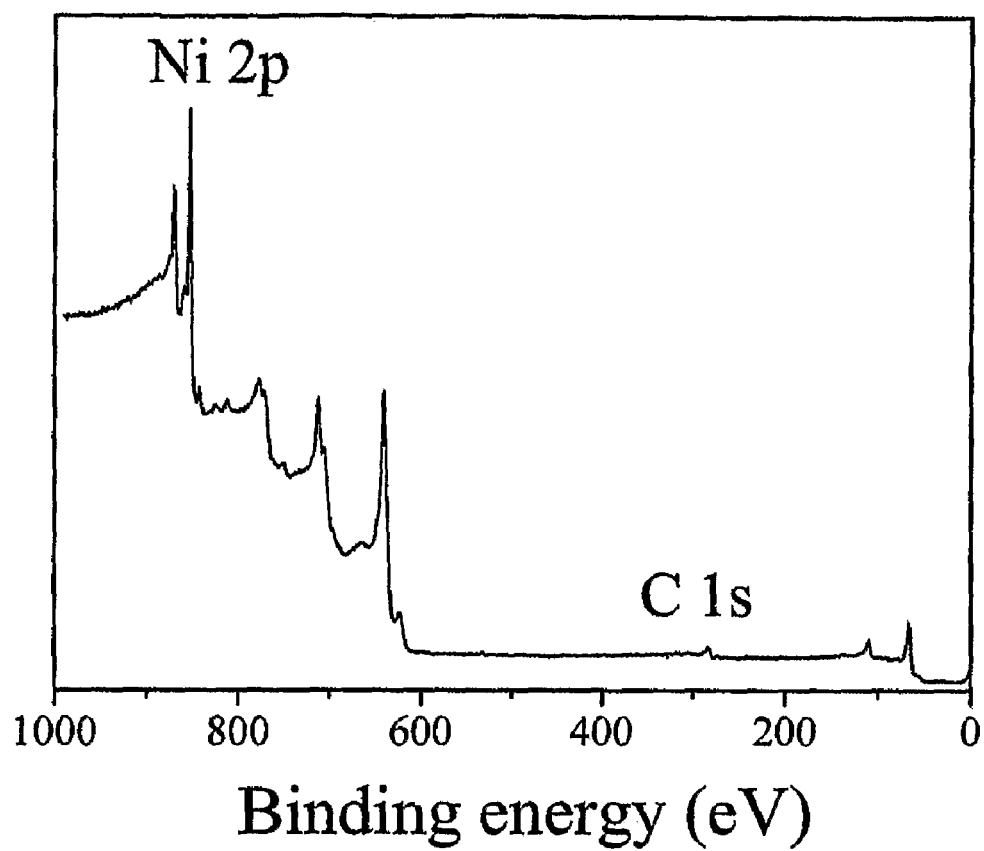
FIG. 10: X-ray photoelectron spectrum of the nickel thin film obtained in Example 6.

An X-ray photoelectron spectrum of the deposited film shown in FIG. 10 confirms that the film was relatively pure metallic nickel containing carbon contaminants in a small amount of 8% or less.

EXAMPLE 7

A Si(001) wafer having an oxide layer on its surface was heated to a temperature selected from 270, 280, 290, 300, 310, 330 and 350° C. at an initial pressure of 2 mTorr. Ni(dmamb)$_2$ prepared in Example 3 was vaporized at 70° C. and the vapor was transported to the surface of the wafer without using a carrier gas at a total pressure of 80 mTorr to deposit a film thereon.

Figure 11A:
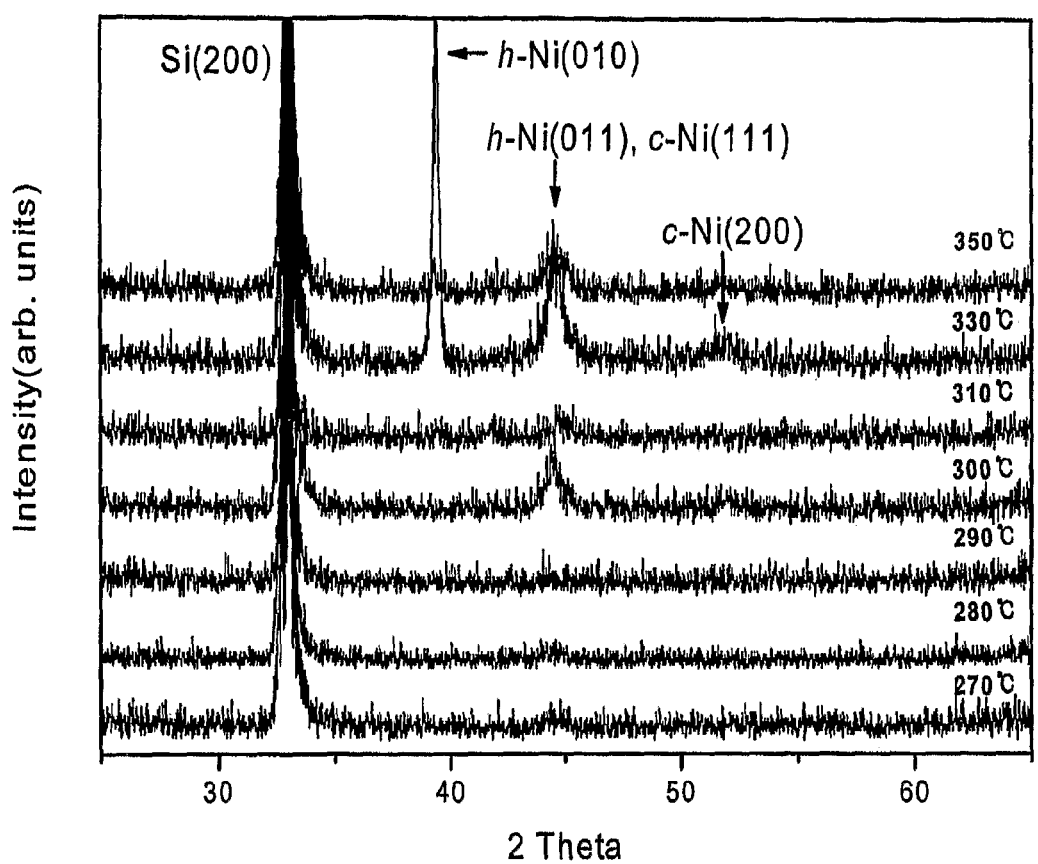
FIGS. 11A and 11B: XRD patterns and SEM images of the nickel thin films obtained in Example 7, respectively.
Figure 11B:
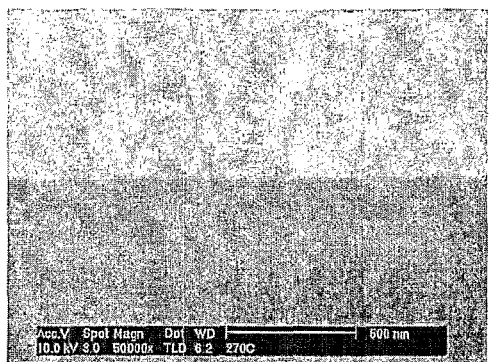
Figure 11B:
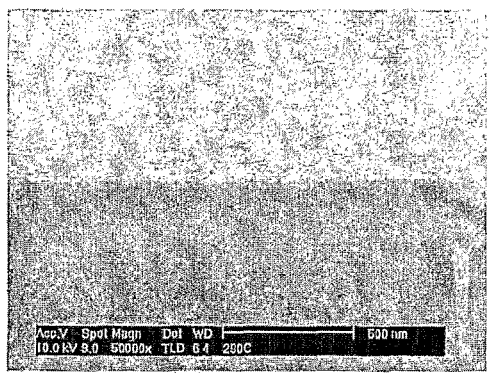
Figure 11B:
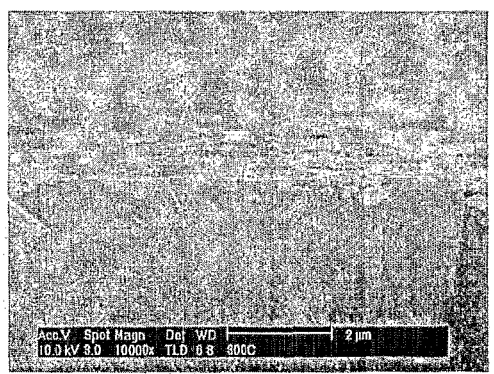
Figure 11B:
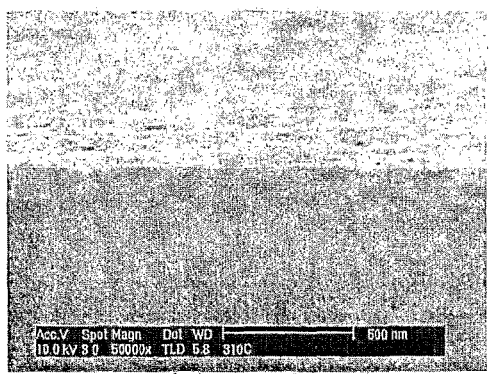
Figure 11B:
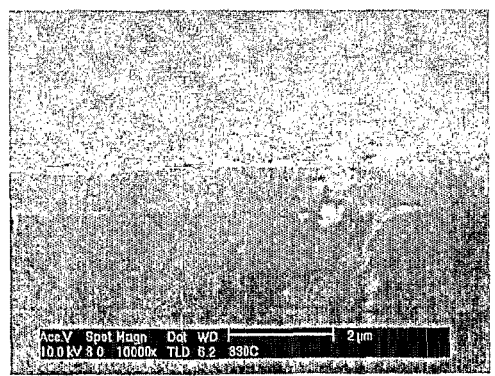
Figure 11B:
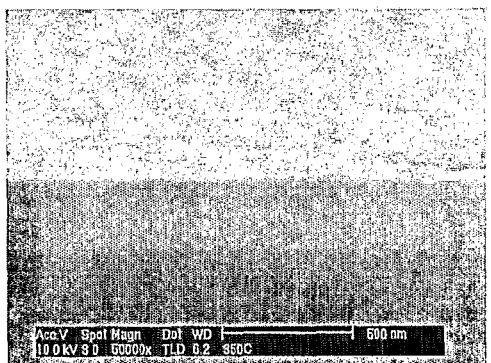

X-ray photoelectron spectra of the deposited films showed that the films were pure metallic nickel. XRD patterns thereof shown in FIG. 11A confirm that the films deposited at 270-310° C. were composed of cubic crystals, and the films deposited at 330-350° C., cubic and hexagonal crystals. SEM images of the films shown in FIG. 11B confirm that dense films were obtained.

As shown above, the nickel complex of the present invention can be vaporized at a low temperature and is thermally stable, and therefore, it may be effectively employed in MOCVD of a nickel thin film having an improved quality.

While the embodiments of the subject invention have been described and illustrated, it is obvious that various changes and modifications can be made therein without departing from the spirit of the present invention which should be limited only by the scope of the appended claims.

What is claimed is:

1. A nickel aminoalkoxide complex of formula (I):

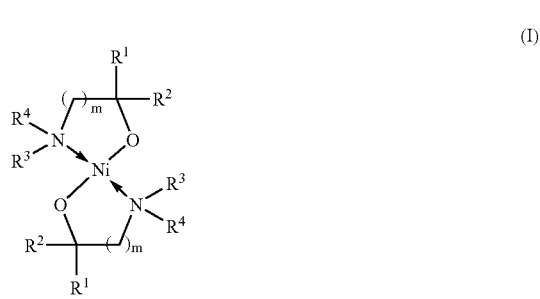

wherein, $R^1$, $R^2$, $R^3$ and $R^4$ are each independently linear or branched $C_{1-4}$ alkyl; and m is an integer in the range of 1 to 3.

2. The compound of claim 1, wherein $R^1$, $R^2$, $R^3$ and $R^4$ are each independently $CH_3$, $C_2H_5$, $CH(CH_3)_2$ or $C(CH_3)_3$, and m is 1 or 2.

3. A process for preparing the compound of claim 1, comprising reacting a compound of formula (II) with a compound of formula (III) in an organic solvent:

$$Ni(OY)_2 \tag{II}$$

$$HOCR^1R^2(CH_2)_m NR^3R^4 \tag{III}$$

wherein, $R^1$, $R^2$, $R^3$, $R^4$ and m are the same as defined in claim 1; and Y is $C_{1-4}$ alkyl.

4. A process for preparing the compound of claim 1, comprising reacting a compound of formula (IV) with a compound of formula (V) in an organic solvent:

$$Ni(NH_3)_6 X_2 \tag{IV}$$

$$MOCR^1R^2(CH_2)_m NR^3R^4 \tag{V}$$

wherein, $R^1$, $R^2$, $R^3$, $R^4$ and m are the same as defined in claim 1; X is halogen; and M is Li or Na.

5. A process for depositing a nickel thin film on a substrate which comprises bringing the vapor of the compound of claim 1 into contact with a substrate heated to a temperature ranging from 200 to 500° C.

6. The process of claim 5, wherein the substrate is heated at a temperature ranging from 250 to 350° C.

7. The process of claim 5, wherein the compound is vaporized at a temperature ranging from 30 to 100° C.

* * * * *